United States Patent [19]

Dugot

[11] Patent Number: 4,600,010

[45] Date of Patent: Jul. 15, 1986

[54] ELECTRIC STIMULATOR AND TEST INSTRUMENT THEREFOR

[75] Inventor: Richard S. Dugot, New York, N.Y.

[73] Assignee: Biolectron, Inc., Hackensack, N.J.

[21] Appl. No.: 657,803

[22] Filed: Oct. 4, 1984

[51] Int. Cl.⁴ ............................................. A61B 5/00
[52] U.S. Cl. ................................. 128/419 F; 128/421
[58] Field of Search ...... 128/419 F, 419 PT, 419 PG, 128/421–423, 702, 704, 903

[56] References Cited

U.S. PATENT DOCUMENTS

| | | | |
|---|---|---|---|
| 3,253,588 | 5/1966 | Vuilleumier et al. | 128/696 |
| 3,807,392 | 4/1974 | Harris | 128/702 |
| 4,024,875 | 5/1977 | Putzke | 128/419 PG |
| 4,115,864 | 9/1978 | Vick et al. | 128/702 |
| 4,250,888 | 2/1981 | Grosskopf | 128/706 |
| 4,276,883 | 7/1981 | McDonald et al. | 128/419 PT |
| 4,360,030 | 11/1982 | Citron et al. | 128/702 |
| 4,459,988 | 7/1984 | Dugot | 128/419 F |
| 4,509,520 | 4/1985 | Dugot | 128/419 F |

*Primary Examiner*—William E. Kamm
*Assistant Examiner*—Mitchell J. Shein
*Attorney, Agent, or Firm*—Brumbaugh, Graves, Donohue & Raymond

[57] ABSTRACT

Body stimulator apparatus comprises a portable housing containing a signal generator that supplies a periodically varying treatment signal of ultrasonic frequency and given voltage and current to electrodes applied to a living body to be treated. A retrievable record of the time of treatment is stored in digital form and the voltage and current are sensed and analog representations thereof are fed to a normally disabled analog to digital converter. The converter is enabled by synchronizing pulses from a separate test instrument and the analog representations converted to digital form are latched and loaded into a shift register array with the stored record of the treatment time and shifted out therefrom serially to the test instrument by clock pulses generated by the latter.

The test instrument is actuatable to generate the synchronizing and clock pulses required to enable the converter and actuate the shift register. The data output from the shift register in the stimulator is stored in a shift register in the test instrument and is selected for display on a display device by actuation of one of several actuator buttons actuatable selectively to retrieve either of the analog representations of the current and voltage or the stored record of the treatment time.

12 Claims, 6 Drawing Figures

```
BIT      1  2  3  4  5  6  7  8  9  10 11 12 13 14 15 16 17 18 19 20 21 22 23 24
200 ( )
DAYS       (MSD              LSD)
VOLTS OVERANGE                    ( )
VOLTS                                 (MSD        LSD)
CURRENT OVERANGE                                      ( )
CURRENT                                                   (MSD        LSD)
LOOSE ELECTRODE                                                              ( )
```

ELECTRIC STIMULATOR AND TEST INSTRUMENT THEREFOR

This invention relates to electrical apparatus for stimulating osteogenesis in a living body, and more particularly to new and improved apparatus of this character comprising a portable, essentially tamper proof electrical stimulator device adapted to be carried by a patient to be treated, and a portable test instrument, accessible only to a person supervising the treatment of the patient, for monitoring multiple operating parameters of the stimulator device selectively in a simple yet highly effective manner.

BACKGROUND OF THE INVENTION

U.S. Pat. No. 4,459,988 for "Electrical Stimulator Apparatus" discloses a system for stimulating osteogenesis in a living body which includes a portable stimulator instrument adapted to be carried by a patient during treatment, and a clinical control instrument adapted to remain in the custody of a physician or other person directing the treatment program for periodically monitoring the condition of the stimulation instrument and for reading out, during a course of treatment, data registered therein.

It is an object of the invention to provide new and improved electrical stimulator apparatus of this general character that is light in weight, low in power consumption, and simple and easy to manufacture and use.

SUMMARY OF THE INVENTION

Stimulator apparatus according to the invention comprises a small, portable housing containing a battery-powered electrical oscillator and amplifier connected to supply an alternating signal of ultrasonic frequency and predetermined current and voltage to electrodes adapted to be mounted on the body of a patient to be treated. Settable timing means in the housing controls the energization of the oscillator and amplifier and other circuits in the housing in accordance with a selected program. The battery voltage and the electrode current and voltage are sensed and means are provided for actuating audible and visible signals to warn the patient in the event the sensed values are inappropriate for proper treatment so that timely remedial action can be taken.

The accumulated time of application of the treatment current to the patient is stored in the form of a digital code in a register in the housing which is responsive to clock pulses from a clock pulse generator.

In order to facilitate retrieval of the sensed electrode voltage and current data by a separate test instrument when desired, the sensed values are fed to an analog to digital (A/D) signal converter in the housing which normally is inactive and not energized. The A/D converter is adapted to be activated and powered upon receipt of a periodically recurring synchronizing signal from the separate test instrument when the stimulator is connected thereto. Each time the A/D converter is so powered, it converts multiplexed analog data representing the sensed electrode current and voltage values into coded digital data which is latched into holding registers in the stimulator. Upon receipt of the next synchronizing signal, the current and voltage data and the treatment time data are loaded into a shift register and shifted out serially to the test instrument in response to clock pulses received from the latter and synchronized with the synchronizing pulses.

Preferably, the control circuit components are incorporated in an integrated circuit chip, the oscillator and its amplifier and certain other components such as reference voltage sources being separately mounted with the chip on a printed circuit board in the housing.

The invention also contemplates the provision of a test instrument connectible to the stimulator for retrieving the current, voltage and treatment data therefrom. To this end, the test instrument incorporates timing logic for generating synchronizing and clock signals for transmission to the stimulator as described above, as well as registers to receive the data shifted serially out of the stimulator and manually actuatable logic to select the data corresponding to each selected quantity to be monitored for transmission to a display driver to cause the value represented by those bits to be exhibited by a display device. As in the stimulator, wherever feasible the circuit components are preferably incorporated in an integrated circuit chip.

DESCRIPTION OF A PREFERRED EMBODIMENT

For a better understanding of the invention, reference is made to the following detailed description of a preferred embodiment, taken in conjunction with the accompanying drawings in which.

Figure 1:
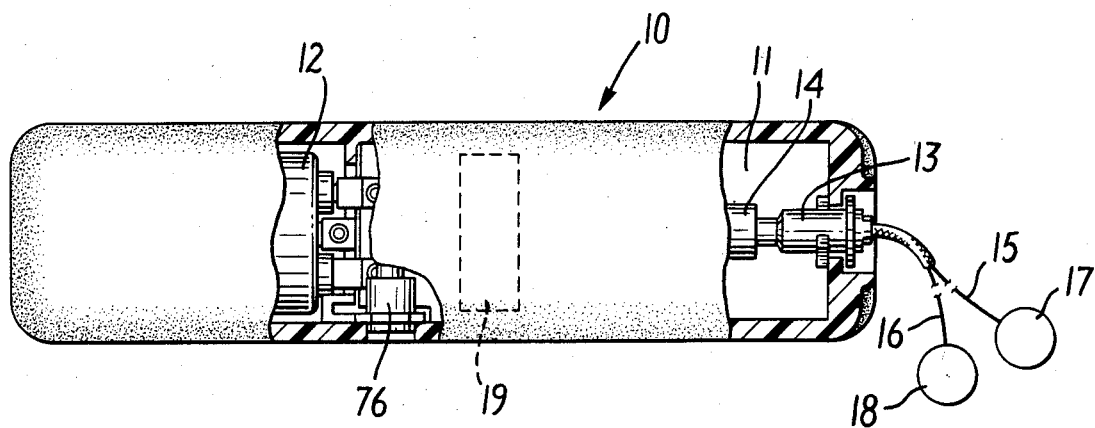
FIG. 1 illustrates schematically a stimulator constructed according to the invention.

Referring first to FIG. 1, electrical stimulator apparatus according to the invention comprises a small, elongated housing 10 containing circuitry mounted on a printed circuit board 11 powered by a small 9 volt battery 12. The stimulator circuitry supplies an alternating signal through a jack plug 13 engaged in a jack socket 14 and the conductors 15 and 16 to electrodes 17 and 18 adapted to be applied to the body of a patient to be treated. In order to conserve space and facilitate manufacture, many of the stimulator circuit components are incorporated in an integrated circuit chip 19 mounted on the printed circuit board 11 in the stimulator housing 10. The chip may be of standard form incorporating, say, eighteen connector pins in a conventional dual-in-line package for connection to other circuit components also mounted on the circuit board 11.

The circuit board components include a conventional electrical oscillator 20 (FIG. 2) designed to generate an alternating signal at an ultrasonic frequency of, say, 60 KHz and a conventional amplifier 20a from which the treatment current is supplied through the conductors 15 and 16 to the treatment electrodes 17 and 18. Application of the treatment current to the electrodes 17 and 18 is controlled by timing logic 21 which sends control signals over the conductor 22 to actuate a transistor switch 23 to control the connection of the oscillator 20 and the amplifier 20a to the battery supply.

Desirably, the timing logic 21 is preferably designed for continuous operation or for intermittent operation at one or the other of several different on-off timing rates. Preferably, tri-state logic is used so that the stimulator may be set selectively for continuous operation, or for intermittent operation with a duty cycle of eight hours on, sixteen hours off, or a duty cycle of two hours on, twelve hours off, depending on whether the pin "5" of the chip is connected to the positive battery supply, to ground, or is left unconnected.

To this end, the timing logic 21 receives timing pulses for the two hours on, twelve hours off condition from a timer 24 which receives pulses at a rate of one every two hours from a counter 25 responsive to one second pulses received from a clock pulse source 26 through a clock gate 27 and the conductor 28. For the eight hours on, sixteen hours off condition, the timing logic 21 receives timing pulses from a timer 29 actuated by pulses at a rate of one every four hours from the counter 25.

The clock pulse source 26 may comprise a conventional oscillator 31 incorporated in the chip 19 and controlled by a 32.768 KHz crystal 32 and resistor 33 connected in parallel to the pins "11" and "12" of the chip 19, and a counter 34 also embodied in the chip for dividing the oscillator frequency down to clock pulses of one per second.

For proper treatment of a patient, it is essential that the source battery voltage and the current to the electrodes be continuously monitored. To this end, the battery voltage is sampled by an internal voltage divider 35 in the chip 19 and fed to one input terminal of a conventional comparator 36 which also receives a reference voltage input over a conductor 37 and the pin "4" of the chip from a potentiometer 38 mounted on the printed circuit board 11. The potentiometer is energized by a constant voltage maihtained by a reference voltage source such as a type AD589JH device 39 also mounted on the printed circuit board 11 and connected through a second reference voltage source 40 and a voltage dropping resistor 41 to the positive battery terminal.

With a 9 volt battery source and the logic 21 providing a control signal in the "1" state, the potentiometer 38 is adjusted so that when the battery voltage drops to about 4.5 volts, the comparator 36 transmits a signal to warning signal logic 42 also incorporated in the chip 19. The logic 42 receives pulses at a rate of, say, one every half-second from the counter 34 over the conductor 43 and, upon receipt of an input signal from the comparator 36, provides a periodically variable signal output of audible frequency at the "7" pin of the chip 19, which causes an external signaling device 44 to generate a steady audible signal and an external LED device 45 to be illuminated. A manually operable switch 46 is provided to disable the audible signalling device if desired.

The current supplied to the treatment electrodes 17 and 18 is sensed across a resistor 47 and is supplied through the "2" pin of the chip and a conventional multiplexer 48 to a conventional amplifier-rectifier 49, both incorporated in the chip 19. The amplifier-rectifier 49 supplies a DC signal representative of the electrode current through a conductor 50 to one input terminal of a conventional comparator 51. The comparator 51 receives a second reference input through the pin "18" of the chip 19 which is connected to a voltage divider 52 shunting the series connected reference voltage sources 39 and 40.

The comparator 51 serves to attenuate the output of the amplifier 20a whenever the treatment current supplied to the electrodes 17 and 18 rises to an undesirable high value. The threshold value of the treatment current is set by the voltage divider 52. When the threshold current value is reached, the comparator 51 delivers a signal to a conventional flip-flop and transmission gate 53 which connects the pin "9" of the chip 19 to ground. The signal output from the oscillator 20 is then attenuated by the ratio of two resistors 54 and 55 external to the chip, thus reducing the current supplied to the electrodes 17 and 18 to a desired value.

The amplifier-rectifier 49 also supplies a DC signal representative of the current in the circuit of the electrodes 17 and 18 over the conductors 50 and 56 to one input terminal of a third comparator 57. The comparator 57 also receives a reference input signal over a conductor 58 and the pin "17" of the chip from a potentiometer 59 mounted on the printed circuit board and connected in shunt with the reference voltage sources 39 and 40 in series. The potentiometer voltage is set such that if the current in the circuit of the electrodes 17 and 18 drops to a very low value indicating a loose electrode or poor electrode contact with the skin of a patient, the comparator 57 will transmit a warning signal over the conductors 60 and 61 to the alarm logic 42. This causes the latter to respond to clock pulses at a rate of, say, one every quarter-second from the counter 32 over the conductor 62 to pulse the audible and visible alarms 44 and 45, respectively, at a different characteristic rate, indicating the existence of a loose electrode condition to an observer.

The accumulated time of application of the current to the skin of a patient is stored in a counter 64 which receives pulses at the rate of one a day over a conductor 65 from a counter 66 responsive to one second clock pulses from the source 26. The counter 64 is configured to provide an output in the form of an eight bit code representative of the treatment time in days. The state of the counter is supplied in parallel to a conventional eight bit register 67, for readout by an external test instrument, as described in greater detail below.

Whenever the current to the electrodes 17 and 18 is cut off, the warning signal from the comparator 57 will disable the gate 27, cutting off the supply of clock pulses to the counter 66 and causing the count therein to remain stationary until the current is restored to the electrodes 17 and 18.

The electrode voltage is sensed across the resistor 68 and is capacitively coupled through a conductor 69 connected to the pin "3" of the chip to the multiplexer 48. In normal operation, the multiplexer 48 passes only the sensed treatment current to the amplifier-rectifier 49. When actuated by interrogating signals from an external test instrument to retrieve the current and voltage data from the stimulator, as described below, the multiplexer 48 supplies signals representative of the sampled electrode voltage and current values alternately to the amplifier-rectifier 49 which, in turn, supplies DC signals representative thereof over a conductor 72 to a conventional analog to digital (A/D) converter 71 incorporated in the chip 19.

The A/D converter 71 is normally disabled and is not enabled until the stimulator is connected to an external test instrument and the latter is set for readout of the current and voltage values being supplied to the electrodes 17 and 18. When that occurs, a sequence of interrogating signals J̄ (FIG. 4) is received from the test instrument through a pin 75 of a connector 76 (FIGS. 1 and 2) adapted to be connected to a cooperating connector on the test instrument as described below, the conductor 77, the pin "15" of the chip, and a conductor 78.

The first interrogating signal J̄ from the conductor 78 actuates a conventional flip-flop 79 which powers the A/D converter 71 over the conductor 80. The A/D converter 71 also receives the interrogating signal directly over the conductors 78 and 81 through a gate 82, so that, as soon as it is powered, it starts converting the analog information it is then receiving to six bit digital information.

The interrogating signal is also supplied through a conductor 83 to the "R" pin of a conventional flip-flop 84, the "Q" pin output of which is fed over a conductor 85 to the multiplexer 48, switching the latter to pass the sensed electrode voltage to the amplifier-rectifier 49. The latter supplies a DC signal representative of the sensed electrode voltage to the A/D converter 71, which converts the signal to a six bit digital number representative thereof and transmits that number over the conductors 86 and 96 to a six bit latch 97. If the sensed voltage reading is over range, the converter 71 will transmit a one bit signal indicative thereof to a one bit latch 98 over the conductors 88 and 99.

At the end of the conversion, the converter 71 generates an end of conversion (EOC) signal, which is transmitted over a conductor 90 to clock the flip-flop 84 and over the conductor 91 to one terminal of a NAND gate 100, the other terminal of which receives the $\overline{Q}$ output of the flip-flop 84. The gate 100 supplies a load signal to the latches 97 and 98 over the conductors 101 and 102, so that the six bit digital output of the converter 71 is stored in the latch 97 and any one bit over-range output is stored in the latch 98.

The change in state of the Q signal produced by the application of the EOC signal to clock the flip-flop 84 switches the multiplexer 48 back to the signal representative of the sensed current and supplies it to the amplifier-detector 49. The converter 71 now converts the current representing DC voltage from the amplifier-detector 49 to a six bit digital number which is supplied over the conductors 86 to a six bit latch 87. In the event the current reading is over range, the converter 71 supplies a signal over a conductor 88 to a one bit over-range latch 89.

When conversion of the sensed electrode current is completed, the converter 71 generates a second EOC signal which is fed over the conductors 90 and 91 to one terminal of a NAND gate 92, the other terminal of which receives the Q signal from the flip-flop 84 over the conductor 93. The gate 92 generates a load signal which is supplied to the latch 87 over the conductors 94 and 95 and causes the output from the converter 71 to be stored in the latch 87. The load signal is also supplied over the conductor 94 to the one bit over-range latch 89, so that an indication of an over-range condition will be stored in the latch 89.

The EOC signals generated by the converter 71 are also fed over the conductors 90 and 103 to a count of two counter 104. Upon receipt of the second EOC signal at the end of the two current and voltage conversions, the counter 104 transmits a reset signal to the flip-flop 79 causing the latter to remove power from the converter 71 until the next interrogating signal is received.

The contents of the latches 87, 89, 97 and 98 are supplied over the conductors 105, 106, 107 and 108, respectively, to the adjacent sections 109, 110, 111 and 112, respectively, of a twenty-four bit shift register 113. Also, the contents of the eight bit counter 64 and the loose electrode signal from the comparator 57 are supplied to the shift register sections 67 and 115, respectively, over the conductors 116 and 117, respectively. The contents of the eight bit counter 64 are also fed over the conductors 118 to a decoder 119 which, when a maximum value of, say, 200 days has been reached, actuates a flip-flop 120 that supplies a signal over a conductor 121 to a one bit end section 122 of the shift register 113.

Figures 3, 4:
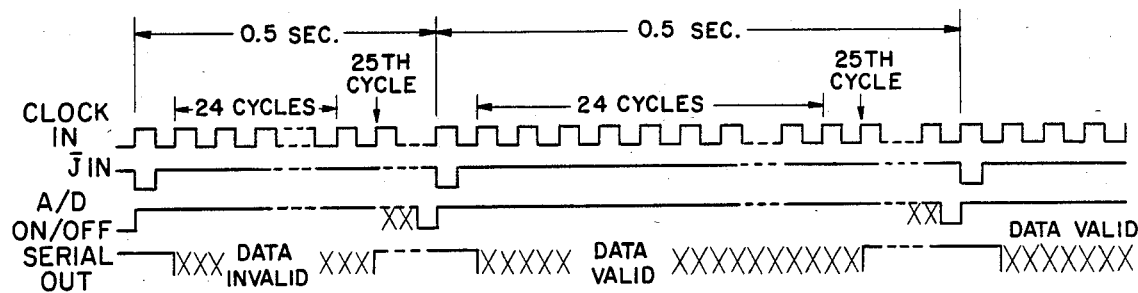
FIG. 3 shows a typical arrangement of the electrode current and voltage and treatment time information generated in the stimulator in the form of a serial digital data stream for transmission to a separate test instrument external to the stimulator.
FIG. 4 is a typical timing diagram illustrating the relation between the interrogating and clock signals from an external test instrument and the operation of the stimulator in retrieving the current, voltage and treatment time information from the latter.

Loading of the register sections 115, 109, 110, 111, 112, 67 and 122 is effected by the interrogating signal J̄ received from the conductor 78 over the conductors 123, 124, 125, 126, 127, 128 and 129, respectively. The loaded shift register 113 then contains a twenty-four bit serial data stream, the order of bits being arranged as shown in FIG. 3, for example. As described in greater detail below, the shift register sections 115, 109, 110, 111, 112, 67 and 122 are also connected to receive clock pulses from an external test instrument over a pin 130 in the connector 76, the "14" pin of the chip, and the conductors 131, 132, 133, 134, 135, 136 and 137, respectively. These clock pulses are generated in timed relation to the interrogating signals J̄ as shown in FIG. 3, for example, and they cause the contents of the shift register 113 to be shifted out serially to an external test instrument over a conductor 139, and the "10" pin of the chip which is connected to a terminal 140 in the connector 76. The bits are shifted out serially in the order illustrated in FIG. 3, bit "1" being shifted out first.

When the day counter 67 registers its maximum count of, say, 200 days, it is automatically disabled from incrementing, and it provides an output to set an over-range bit in the shift register section 122, as stated. This output is also supplied over the conductor 141 to the timing logic 21 to cause the latter to disable the oscillator 20, the amplifier 20a, and the comparators 51 and 57.

The Test Instrument

Figure 5:
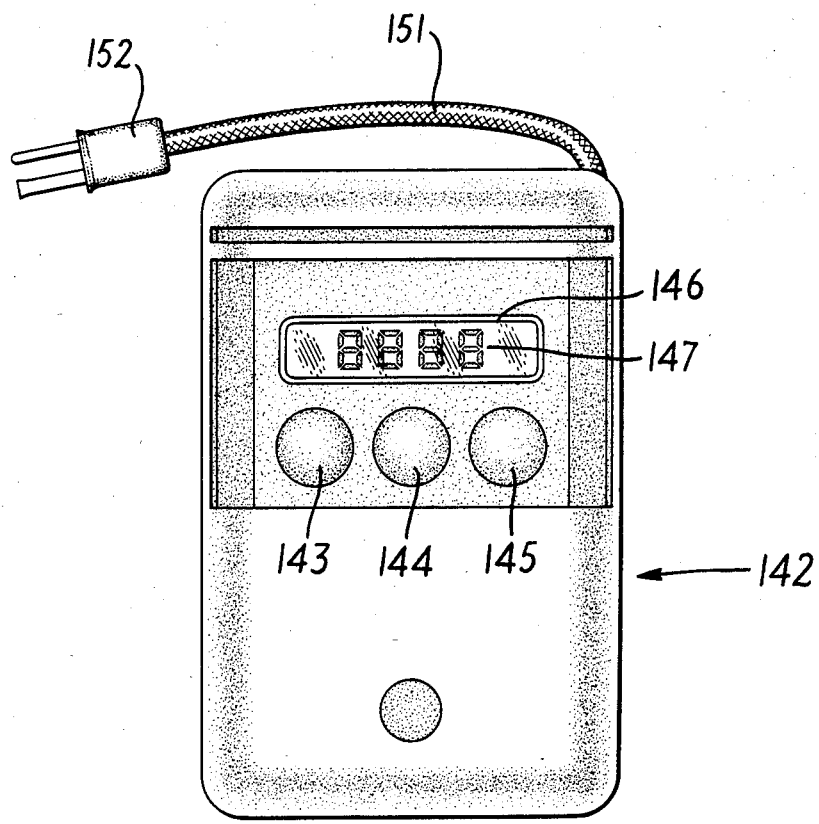
FIG. 5 illustrates schematically a test instrument constructed according to the invention for retrieving current, voltage and treatment time information from the stimulator shown in FIG. 1.
Figure 6:
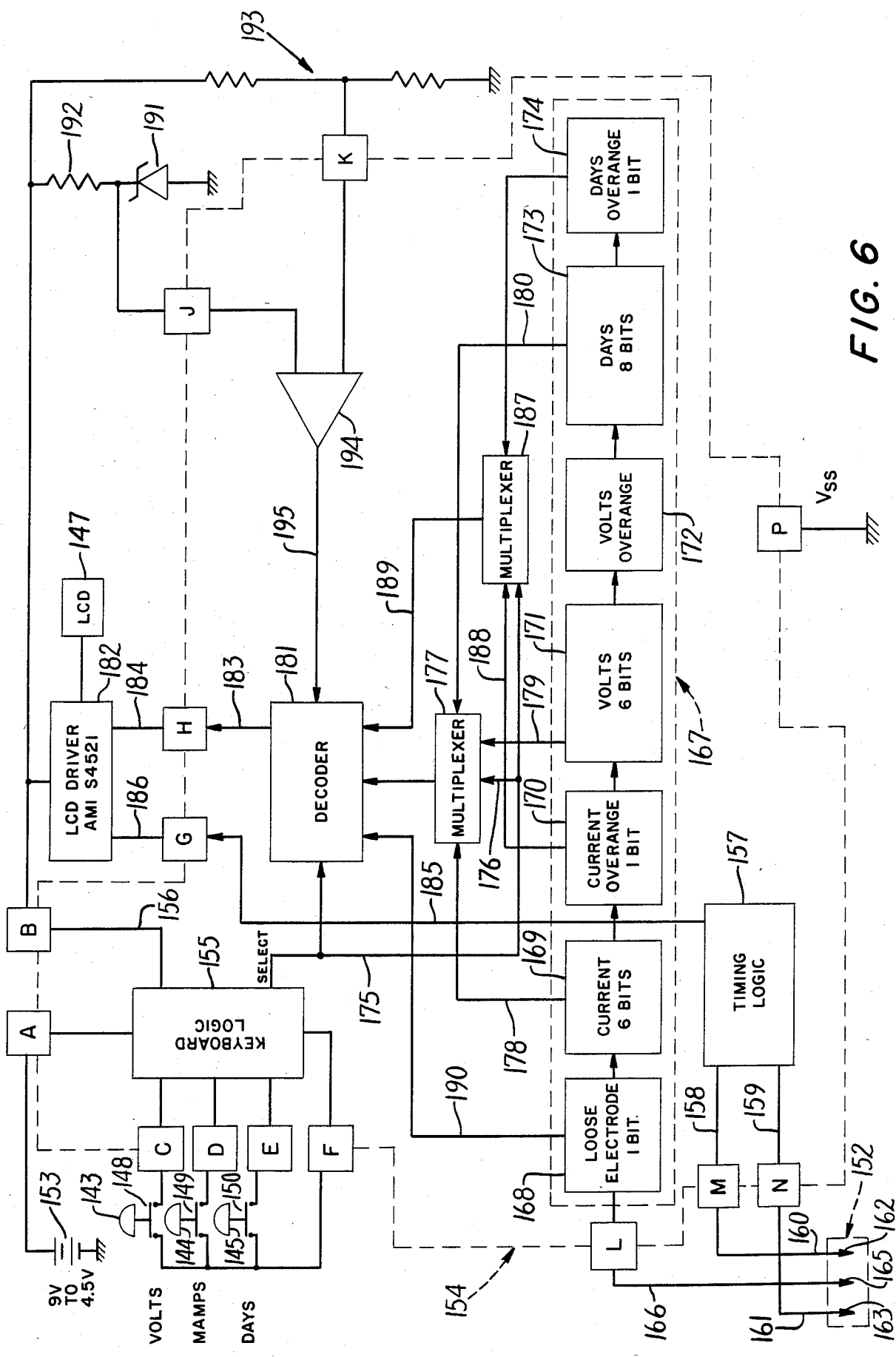
FIG. 6 is a schematic diagram illustrating the circuitry contained in the test instrument shown in FIG. 5.

Periodically during the treatment of a patient with current from the stimulator, it is desirable to check certain operating features such as the electrode current and voltage, and to read out the accumulated treatment time to the date of the test. A typical test instrument according to the invention for this purpose is illustrated in FIGS. 5 and 6. It comprises a case 142 having three pushbuttons 143, 144 and 145 mounted on the front wall thereof below a window 146 through which data displayed on an LCD device 147 can be viewed. The pushbuttons 143, 144 and 145 are adapted to be depressed selectively when it is desired to read out the "Voltage," "Current" and "Days" data from the stimulator and they actuate switches 148, 149 and 150, respectively (FIG. 6), which are connected in electrical circuits contained within the case 142. Electric signals from the stimulator are adapted to be fed to those circuits through conductors in a cable 151 connected to a plug 152 (FIGS. 5 and 6) connectible to the connector 76 (FIGS. 1 and 2) of the stimulator.

Referring now to FIG. 6, the test instrument may be powered by a conventional 9 volt battery 153 in the case 142, having its negative terminal connected to ground and its positive terminal connected to the pin "A" of a chip 154 in which most of the circuit components are incorporated. The switches 148, 149 and 150 are connected to the pins "C", "D", "E" and "F" of the chip 154 as shown. The pins "C", "D", "E" and "F" of the chip are connected to keyboard logic 155 which, when any one of the pushbuttons 143, 144 and 145 is depressed, powers the chip 154 circuit components from the pin "A" of the chip, and also connects the positive battery terminal to the pin "B" of the chip by a conductor 156 to provide voltage for circuit components external to the chip, as described below.

The keyboard logic 155 is preferably designed in the known manner so that, if multiple pushbuttons are depressed simultaneously, it will select the function having the highest priority, the desired order of priority being voltage, current and accumulated days of treatment registered by the stimulator.

So long as any pushbutton is depressed, timing logic 157 in the chip 154 is energized by the battery 153 through the keyboard logic 155. The timing logic 157 supplies clock signals over a conductor 158 to the pin "M" of the chip and interrogating signals J̄ over a conductor 159 to the pin "N" of the chip, the clock and interrogating signals having the relationship shown in FIG. 4, for example. The pins "M" and "N" of the chip are connected by conductors 160 and 161, respectively, in the cable 151 to the pins 162 and 163, respectively, of the plug 152 (FIGS. 5 and 6).

When interrogated, the stimulator generates a twenty-four bit data stream output which is received at a pin 165 in the plug 152 and is fed by a conductor 166 to the pin "L" of the chip. From the pin "L" of the chip, the twenty-four bit data stream is entered in a data register 167 incorporated in the chip 154. The register 167 has sections 168 through 174, corresponding to the sections 115, 109, 110, 111, 112, 67 and 122, respectively, of the register 113 (FIG. 2) in the stimulator, which receive the data bits in the same order that they were entered in the register 113.

Actuation of any one of the pushbuttons 143, 144 and 145 also results in the transmission of a corresponding two bit "select" signal from the keyboard logic 155 over the conductors 175 and 176 to a multiplexer 177. The multiplexer 177 receives the appropriate current, voltage or days representing bits over the conductors 178, 179 and 180, respectively, and transmits the selected group to a decoder 181 incorporated in the chip 154. The decoder 181 converts the received data to signals appropriate for actuation of a driver 182 such as an AMI type S4521 to energize the LCD display device 147 in the case 142. The data representing signals are supplied serially to the pin "H" of the chip over a conductor 183 and then to the driver 182 over a conductor 184. The driver 182 also receives a load signal from the timing logic 157 over the conductors 185 and 186 and the pin "G" of the chip.

If, when the current selection pushbuttom 149 is depressed, the data stream output from the stimulator contains a bit representing an over-range condition for the parameter selected, it is desired that the display device 147 exhibit a perceptible indication of this condition. To this end, a select code from the keyboard logic 155, transmitted over the conductors 175, enables a multiplexer 187 to transmit the over-range bit over the conductors 188 and 189 to the decoder 181. Circuitry in the latter causes the display device 147 to produce a flashing "888" display. A similar display is produced when either the "Volts" pushbutton 143 or the "Days" pushbutton 145 is depressed and the data stream includes an over-range "Volts" or "Days" bit.

In the event the data stream from the stimulator contains a bit representing an under-range current condition indicating, e.g., a loose electrode, that bit is transmitted over the conductor 190 to the decoder 181 and circuitry in the latter will then produce a blinking "∅∅∅" display on the display device 147.

Desirably, a perceptible signal should be produced by the test instrument when the voltage from its battery source drops below a predetermined value. For this purpose, a reference voltage is established across a conventional external voltage regulator device 191, e.g., a zener diode, connected in series with an external resistor 192 between the positive battery supply and ground. This voltage is supplied to the pin "J" of the chip. Also, the battery voltage is sampled by a voltage divider 193, also connected between the positive battery voltage and ground, and is supplied to the pin "K" of the chip.

The reference voltage and the sampled voltage are supplied from the pins "J" and "K" of the chip to the input terminals of a comparator 194 incorporated in the chip 154. When the sampled voltage drops to a predetermined value in relation to the reference voltage, the comparator 194 provides a signal output to the decoder 181 over the conductor 195 and causes circuitry therein to activate the driver 182 to illuminate a "Low Batt" display in the display device 147.

Operation

The stimulator is prepared for operation by connecting the pin "5" of the chip (FIG. 2) either to the positive voltage supply or to ground or leaving it unconnected, depending on the duty cycle desired for the treatment current. The electrodes 17 and 18 are then mounted at the desired locations on the body of the patient to be treated, in the usual manner. A standby battery 196, which may be a conventional 3 volt lithium battery for example, is then connected between the positive voltage supply terminal and the pin "13" of the chip. The standby battery voltage is supplied over a conductor to the day counter 64 so that the latter is powered continuously, even when the main battery power supply is removed.

A conventional 9 volt battery is inserted in the stimulator casing with its positive terminal connected to the pin "16" of the chip and its negative terminal connected to ground. This causes the timing logic 21 to be set to the selected state. In this state, the oscillator 20 generates an alternating signal at a frequency of, say, 60 KHz, which is amplified by the amplifier 20a and supplied to the electrodes 17 and 18. Also, the amplifier-rectifier 49 is now activated and supplies a signal representative of the electrode current to the loose electrode comparator 57. The low battery comparator 36, the attenuator comparator 51, the clock pulse source 26, and the warning signal logic 42 are all enabled, but the A/D converter 71 is disabled. The prescribed treatment current will then continue to be supplied to the electrodes 17 and 18 and the accumulated treatment time will continue to be registered in the counter 64 in units of days.

If the timing logic 21 was initially set for intermittent operation, with a duty cycle of, e.g., 8 hours on, 16 hours off, the external oscillator 20, the amplifier 20a, the warning signal logic 42, and the comparators 36, 51 and 57 will all be temporarily disabled at the end of each duty cycle. The loose electrode comparator 57 and the gate 27 are also disabled, so that the counter 64 stops counting. The timing logic 21, however, will cause restoration of the initial operating conditions at the expiration of the "Off" period.

If, while the stimulator is on, the electrode current drops below the desired value, because of a loose or disconnected electrode for example, the warning signal logic 42 will cause the audible alarm 41 to sound at a characteristic rate. Also, if the battery voltage drops to, say, 4.5 volts, the alarm 44 will produce a continuous tone until the 9 volt battery is replaced or the battery voltage drops below that required for operation. Preferably, the low battery alarm has first priority.

In the event the treatment current rises above the value for which the potentiometer 52 is set, the attenuator comparator 51 will transmit an output signal to the flip-flop 53, causing the latter to connect the pin "9" of the chip to ground. This results in attenuation of the 60 KHz signal supplied to the amplifier 20a by the ratio of the resistors 54 and 55, and this condition continues until the flip-flop 53 is reset when a new battery is installed.

So long as the battery voltage and electrode current are within specified limits, the counter 64 registers the accumulated time of application of the electrode current in days in the form of an eight bit digital code.

Figure 2:
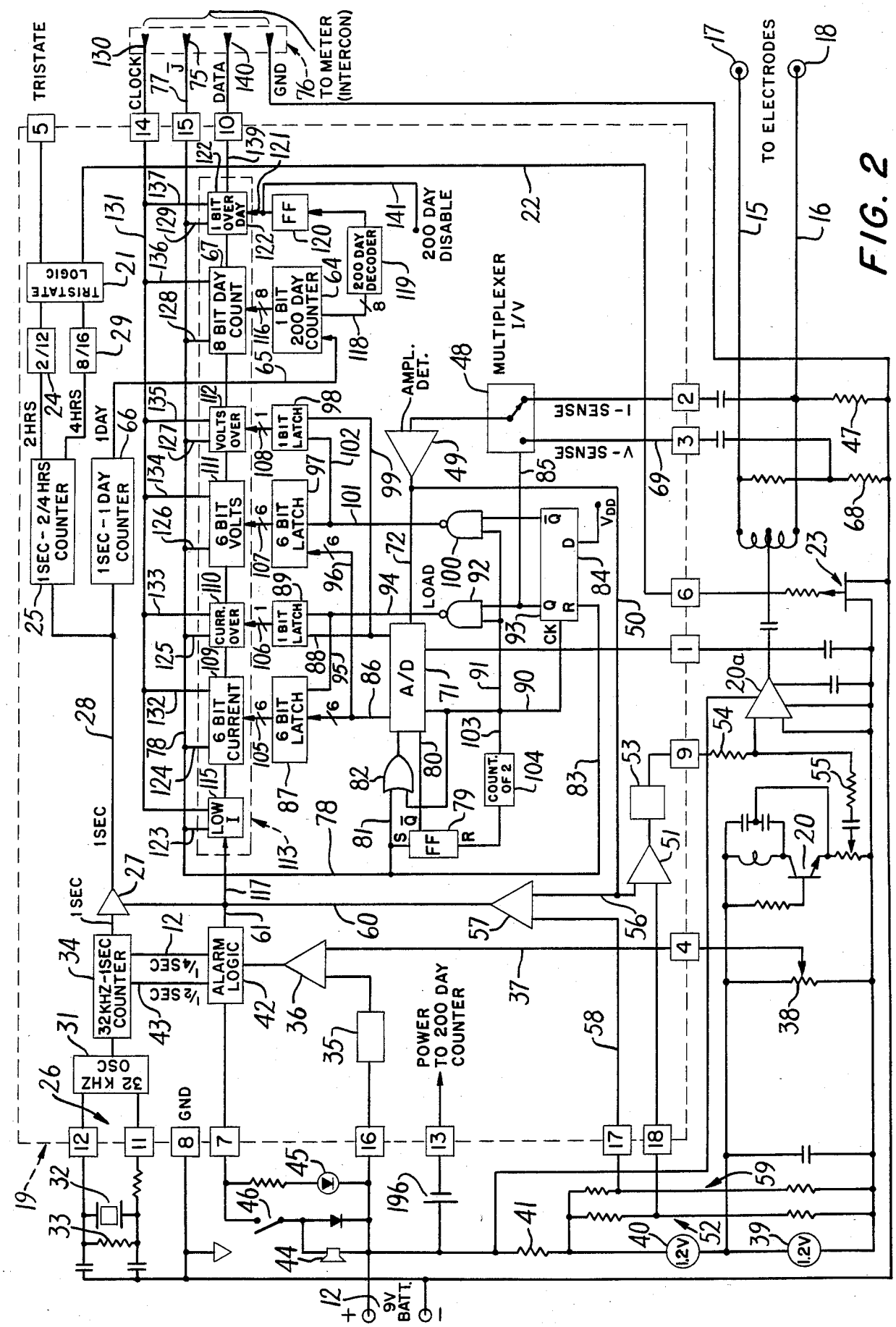
FIG. 2 is a schematic diagram of typical electrical circuits contained in the stimulator shown in FIG. 1.

In the usual practice, a new 9 volt battery will be installed every twenty-four hours and whenever information is to be retrieved from the stimulator. Also, the patient will be examined periodically, say once a month, by a doctor or technician to ascertain the progress of the treatment. At that time, the treatment time in days, the electrode current and the voltage can be read out of the stimulator by first installing a new battery in the latter and inserting the test instrument plug 152 (FIGS. 5 and 6) in stimulator socket 76 (FIGS. 1 and 2).

To retrieve, say, the current data from the stimulator, the current pushbutton 144 on the test instrument is depressed. This causes 1 KHz clock signals and a sequence of interrogating signals J̄ related as illustrated in FIG. 4 to be fed to the connector terminals 130 and 75, respectively. The interrogating signals are supplied over the conductor 78 to power and start the A/D converter 71 and to control the multiplexer 48 and its associated circuitry to cause digital information about the electrode current and voltage values to be loaded into the latches 87, 89, 97 and 98 in response to each interrogating signal.

The next interrogating signal J̄ received over the conductor 75 after data have been stored in the latches 87, 89, 97 and 98 loads that data into the shift register sections 109, 110, 111 and 112, respectively, and the data representative of the state of the day counter 64 into the shift register sections 67 and 122. If a low current condition exists, the output of the low current comparator will enter a bit indicative thereof into the shift register section 115. Clock pulses received from the test instrument over the conductor 130 then output the data contained in the shift register serially over the conductor 140 to the test instrument, where it is entered in registers in the latter.

In the test instrument, the keyboard logic 155 controls the multiplexer 177 in response to actuation of pushbutton 144 to select the data bits corresponding to the current then being monitored and transmit them to the display driver 182 for display on the display device 147.

It will be understood that the data shifted out of the shift register 113 in response to the first interrogating signal J̄ received from the test instrument may not be valid since it will usually represent data taken at some time in the past. The data shifted out in response to all interrogating signals J̄ after the first, however, will be valid. The timing logic 157 (FIG. 6) should, of course, repeat at a rate such that the display on the display device 147 is stable.

A typical system according to the invention may be designed so that the twenty-four bit data stream comprises, for example, an eight bit quantity corresponding to a maximum of 255 days with a one day resolution, a six bit quantity corresponding to a maximum of 6.3 volt peak-to-peak with a resolution of 0.1 voltage peak-to-peak, a six bit quantity corresponding to a maximum of 12.6 milliamps with a resolution of 0.2 milliamps RMS, and three over-range bits for volts, current and days. An over-range condition is denoted by a blinking "888" display and an under-range condition by a blinking "∅∅∅" display.

Preferably, the stimulator is designed so that whenever a new battery 12 is installed, all resettable circuits including the attenuator flip-flop 53, the control logic 21, and all counters will be reset. Also, after the counter 64 has reached its counting limit and has ceased incrementing, it is reset by momentarily breaking the contact between the standby battery 196 and the pin "13" of the chip.

The invention thus provides a simple yet highly effective stimulator device for stimulating osteogenesis in a living body. By continuously sensing the battery voltage and electrode current and immediately generating a perceptible signal whenever inappropriate values are sensed, prompt corrective action can be taken so that treatment of the patient can be carried out most efficiently. Also, by employing normally disabled analog-to-digital converter apparatus and normally disabled shift register means for transmitting to an external test instrument coded digital information representative of data in the stimulator, the construction of the device is simplified and the power requirements are reduced.

The embodiment described in detail herein is intended only to be illustrative. It will be readily apparent to those skilled in the art that modifications in form and detail are possible within the scope of the following claims.

I claim:

1. Portable, light weight apparatus for treating a living body comprising signal generator means for generating a treatment signal, means connected to said signal generator means for applying said treatment signal to a living body to be treated, and means for providing indications of at least one operation condition of said apparatus, wherein the improvement comprises normally disabled means responsive, when enabled, to said operating condition of said apparatus for generating a retrievable representation of said operating condition, said last named means including means for storing said retrievable representation temporarily and being arranged to be enable by transmission thereto of an interrogating signal from an external source connectible to the apparatus, and means arranged to be rendered operative by signals from said external source for transmitting a retrievable representation stored by said storing means as an output from the apparatus.

2. Apparatus for treating a living body as described in claim 1 in which the signal generator means is arranged to generate a periodically varying treatment signal of ultrasonic frequency and given current and voltage, means is provided for sampling at least one of the treatment current and voltage applied to a living body by said applying means and for providing an analog representation thereof, and the means for generating said retrievable representation comprises means for converting said analog representation to a digital code representative of said sampled one of said current and voltage.

3. Apparatus for treating a living body as described in claim 2 in which means is provided for sampling and providing separate analog representations of both the treatment current and the treatment voltage applied to a living body by said applying means, said retrievable representation generating means comprises means for converting said separate analog representations to digital coded data representative of the sampled current and voltage, and said storing means is arranged to store said coded digital data, said transmitting means being arranged to be rendered operative by signals from said external source for transmitting digital coded data stored in said storing means as an output from the apparatus.

4. Apparatus for treating a living body as described in claim 2 in which the means for generating said retrievable representation comprises normally disabled analog to digital converter means connected to received said analog representation, means responsive to a synchronizing signal from said external source for enabling said analog to digital converter means and initiating a first conversion cycle thereof, latching means connected to receive the output of said analog to digital converter means, means responsive to the end of said conversion cycle for loading the output of said analog to digital converter means into said latching means, shift register means connected to receive the contents of said latching means, means responsive to a successive synchronizing signal from said external source for loading the contents of said latching means into said shift register means, and means responsive to clock pulses from said external source occurring in timed relation to said synchronizing signals for actuating said shift register means to shift the contents thereof serially out of said shift register means for retrieval.

5. Apparatus for treating a living body as described in claim 2 in which the means for generating said retrievable representation comprises normally disabled analog to digital converter means, multiplexer means actuatable to pass an analog representation of one of said treatment current and voltage to said analog to digital converter means for conversion thereby, means responsive to a synchronizing signal from said external source for enabling said analog to digital converter means and initiating a first conversion cycle thereof, first and second latching means connected to receive the output of said analog to digital converter means, means responsive to the end of said first conversion cycle for loading the output of said analog to digital converter means into said first latching means, means responsive to the end of said first conversion cycle for actuating said multiplexer means to pass an analog representation of the other of said treatment current and voltage to said analog to digital converter means for conversion thereby and for initiating a second conversion cycle thereof, means responsive to the end of said second conversion cycle for loading the output of said analog to digital converter means into said second latching means, means responsive to the end of said second conversion cycle for disabling said analog to digital converter means, shift register means connected to receive the contents of said first and second latching means, means responsive to a successive synchronizing signal from said external source for loading the contents of said first and second latching means into said shift register means, and means responsive to clock pulses occurring in timed relation to said synchronizing signals from said external source for actuating said shift register means to shift the contents thereof serially out of said shift register means for retrieval.

6. Apparatus for treating a living body as described in claim 1 in which means is provided for accumulating a retrievable record of the treatment by the treatment signal, said accumulating means including timing means and means responsive thereto and operative while said treatment signal is being applied to a body to be treated for generating a digital coded quantity representative of the time of application of said treatment signal to the body to be treated, and said transmitting means is arranged to transmit said digital coded quantity as an output from the apparatus, said last named means being rendered operative by signals from said external source.

7. Apparatus for treating a living body as described in claim 4 in which the signal generator means is arranged to generate a periodically varying treatment signal of ultrasonic frequency and given current and voltage, means is provided for sampling both said treatment current and said treatment voltage and for providing separate analog representations of said sampled treatment current and voltage; the means for generating said retrievable representation comprises means for converting said analog representations to digital coded quantities representative, respectively, of said treatment current and treatment voltage; the storing means is arranged to store said digital quantities temporarily; and said transmitting means comprises register means for transmitting the digital coded data representative of said time of application of said treatment signal to the body and said treatment current and treatment voltage as an output from said apparatus, said converting means, storing means and said register means being rendered operative by signals from said external source.

8. Apparatus for treating a living body as described in claim 4 in which the means for generating said retrievable representation comprises normally disabled analog to digital converter means, multiplexer means actuatable to pass an analog representation of one of said treatment current and voltage to said analog to digital converter means for conversion thereby, means responsive to a synchronizing signal from said external source for enabling said analog to digital converter means and initiating a first conversion cycle thereof, first and second latching means connected to receive the output of said analog to digital converter means, means responsive to the end of said first conversion cycle for loading the output of said analog to digital converter means into said first latching means, means responsive to the end of said first conversion cycle for actuating said multiplexer means to pass an analog representation of the other of said treatment current and voltage to said analog to digital converter means for conversion thereby and for initiating a second conversion cycle thereof, means responsive to the end of said second conversion cycle for loading the output of said analog to digital converter means into said second latching means, means responsive to the end of said second conversion cycle for disabling said analog to digital converter means, shift register means connected to receive the contents of said first and second latching means and the digital coded quantity representative of the time of application of said treatment signal to the body to be treated, means responsive to a successive synchronizing signal from said external source for loading the contents of said first and second latching means and said digital coded quantity into said shift register means, and means responsive to clock pulses from said external source occurring in timed relation to said synchronizing signals for actuating said shift register means to shift the contents thereof serially out of said shift register means for retrieval.

9. In combination, apparatus for treating a living body comprising signal generator means for generating a treatment signal, means connected to receive said treatment signal for application thereof to a living body to be treated, means for providing indications of at least one operating condition of said apparatus, normally disabled means responsive, when enabled to said operating condition of said apparatus for generating a retrievable representation of said operating condition, said normally disabled means including means for storing said retrievable representation temporarily, means for transmitting a retrievable representation stored by said storing means as an output from the treating apparatus, and a test instrument connectible to said treatment apparatus, said test instrument comprising manually actuatable means for generating and supplying to said treatment apparatus first signals to enable said normally disabled means to generate a signal representative of said operating condition and second signals to render said output transmitting means effective to transmit said retrievable representation to said test instrument, and means in said test instrument for displaying an output responsive to said retrievable representation.

10. Apparatus as described in claim 9 in which the signal generating means in the treatment apparatus is arranged to generate a treatment signal of ultrasonic frequency and given current and voltage and normally disabled means is provided for generating digital coded quantities representative of said current and voltage and for temporarily storing said digital coded quantities, with normally inoperative means for transmitting digital coded quantities stored in said storing means as outputs of the treatment apparatus; and the test instrument comprises manually actuatable means for generating and supplying to the treatment apparatus first signals for enabling said normally disabled means to generate said digital coded quantities, and second signals to render said normally inoperative means operative to transmit said digital coded quantities stored in said storing means selectively to the test instrument, and means in the test instrument for displaying an output responsive to a selected one of said digital quantities.

11. Apparatus as described in claim 10 together with means for accumulating a retrievable record of the treatment of said body by said treatment signal, and normally inoperative means for transmitting a retrievable record of the treatment of said body stored in said accumulating means as an output of said apparatus, said last named transmitting means being rendered operative by said second signals from said test instrument.

12. Test apparatus connectible to body stimulator treatment apparatus comprising means for providing indications of at least one operating condition of said apparatus, normally disabled means responsive, when enabled, to said operating condition of said stimulator apparatus for generating a retrievable representation of said operating condition, said normally disabled means including means for storing a retrievable representation temporarily, and means for transmitting a retrievable representation stored by said storing means as an output from the treatment apparatus, for retrieving said retrievable representation, comprising manually actuatable means for generating and supplying to said treatment apparatus first signals to enable said normally disabled means to generate a signal representative of said operating condition and second signals to render said output transmitting means effective to transmit said retrievable representation to said test apparatus, register means connected to receive said transmitted retrievable representation, display means, and means responsive to said actuatable means for causing said retrievable representation received by said register means to be displayed by said display means.

* * * * *

UNITED STATES PATENT AND TRADEMARK OFFICE
CERTIFICATE OF CORRECTION

PATENT NO. : 4,600,010
DATED : July 15, 1986
INVENTOR(S) : Richard S. Dugot

It is certified that error appears in the above-identified patent and that said Letters Patent is hereby corrected as shown below:

Column 10, line 64, "enable" should read --enabled--;

Column 12, line 40, "claim 4" should read --claim 6--;

Column 12, line 60, "claim 4" should read --claim 6--.

Signed and Sealed this

Twenty-fifth Day of November, 1986

Attest:

DONALD J. QUIGG

Attesting Officer

Commissioner of Patents and Trademarks